US009921316B2

(12) United States Patent
Qu et al.

(10) Patent No.: US 9,921,316 B2
(45) Date of Patent: Mar. 20, 2018

(54) THERMAL MANAGEMENT SYSTEM, AN X-RAY DETECTION DEVICE AND A COMPUTERIZED TOMOGRAPHY APPARATUS

(71) Applicant: GE Medical Systems Global Technology Co. LLC, Waukesha, WI (US)

(72) Inventors: Weimin Qu, Beijing (CN); Duzi Huang, Beijing (CN); Qun Xing Zhang, Beijing (CN)

(73) Assignee: GE Medical Systems Global Technology Co. LLC, Waukesha, WI (US)

( * ) Notice: Subject to any disclaimer, the term of this patent is extended or adjusted under 35 U.S.C. 154(b) by 342 days.

(21) Appl. No.: 14/621,980

(22) Filed: Feb. 13, 2015

(65) Prior Publication Data
US 2015/0276943 A1    Oct. 1, 2015

(30) Foreign Application Priority Data
Mar. 26, 2014    (CN) .......................... 2014 1 0114335

(51) Int. Cl.
*A61B 6/00* (2006.01)
*G01T 1/24* (2006.01)
*G01N 23/04* (2018.01)

(52) U.S. Cl.
CPC .......... *G01T 1/244* (2013.01); *G01N 23/046* (2013.01)

(58) Field of Classification Search
CPC ...... G01T 1/244; G01N 23/046; A61B 6/035; A61B 6/4488

USPC .................................................. 378/199, 200
See application file for complete search history.

(56) References Cited

U.S. PATENT DOCUMENTS

| | | | | |
|---|---|---|---|---|
| 7,102,308 | B2* | 9/2006 | Lacey | F04D 27/004 318/268 |
| 7,887,237 | B2* | 2/2011 | Krug | A61B 6/035 378/199 |
| 2005/0287008 | A1* | 12/2005 | Lacey | F04D 27/004 417/32 |
| 2006/0109956 | A1* | 5/2006 | Lacey | A61B 6/035 378/199 |
| 2011/0228910 | A1* | 9/2011 | Gregerson | A61B 6/4488 378/200 |

FOREIGN PATENT DOCUMENTS

CN    104337533 A    2/2015

* cited by examiner

*Primary Examiner* — Courtney Thomas

(57) ABSTRACT

The present invention provides a thermal management system, an X-ray detection device and a CT apparatus. The thermal management system comprises a heater, an air mixing portion and a fan. The heater is provided at an air inlet of the air mixing portion. The air mixing portion provides an air mixing space for mixing exterior air that enters the air mixing portion with interior air of the air mixing portion. The fan is provided at an air outlet of the air mixing portion, and supplies the mixed air in the air mixing portion to a target object to be thermally managed. Therefore, a response time of the thermal management system to operate for an external temperature change may be lengthened, thus occurrence of abrupt change in a temperature of the target object as the external temperature changes abruptly may be avoided, improving a reliability of the thermal management system.

14 Claims, 2 Drawing Sheets

THERMAL MANAGEMENT SYSTEM, AN X-RAY DETECTION DEVICE AND A COMPUTERIZED TOMOGRAPHY APPARATUS

FIELD

The present invention relates to a medical imaging field, and more particularly to a thermal management system, an X-ray detection device and a computerized tomography apparatus.

BACKGROUND

A computerized tomography (CT) apparatus usually comprises an X-ray generation device and an X-ray detection device. The X-ray generation device generates X-rays and emits the generated X-rays to an object to be scanned. The X-ray detection device receives the X-rays penetrating the object to be scanned and converts the received X-rays to electric signals. Furthermore, a CT apparatus may also comprise an image processor for processing the electric signals converted by the X-ray detection device to produce an image of the object to be scanned and a display for displaying the produced image.

Usually, the X-ray detection device needs to be operated under a condition of appropriate temperature, so as to eventually obtain an image having a desired quality. Therefore, in order to ensure the quality of the obtained image, the CT apparatus further comprises a thermal management system for thermally managing the X-ray detection device.

SUMMARY

An objective of exemplary embodiments of the present invention lies in overcoming the above and/or other defects in the prior art. Accordingly, the exemplary embodiments of the present invention provide a thermal management system, an X-ray detection device and a CT apparatus, which have an improved reliability.

According to an exemplary embodiment, a thermal management system is provided, which comprises a heater, an air mixing portion and a fan. The heater is provided at an air inlet of the air mixing portion, and is configured to heat air when exterior air enters the air mixing portion via the air inlet. The air mixing portion is configured to provide an air mixing space for mixing the exterior air that enters the air mixing portion with interior air of the air mixing portion. The fan is provided at an air outlet of the air mixing portion, and is configured to supply the mixed air in the air mixing portion to a target object to be thermally managed.

According to another exemplary embodiment, an X-ray detection device is provided, comprising: an X-ray detector configured to receive X-rays and convert the received X-rays to electric signals; a thermal management system as stated above, which performs a thermal management on the X-ray detector as the target object.

According to another exemplary embodiment, a CT apparatus is provided, comprising: an X-ray generation device configured to generate X-rays and emit the generated X-rays to an object to be scanned; an X-ray detection device as stated above, configured to receive the X-rays penetrating the object to be scanned and convert the received X-rays to electric signals.

Other features and aspects will become apparent from the detailed description, the accompanying drawings and claims that follow.

BRIEF DESCRIPTION OF THE DRAWINGS

The present invention can be understood better in light of the description of exemplary embodiments of the present invention with reference to the accompanying drawings, in which.

DETAILED DESCRIPTION

Hereafter, a detailed description will be given for preferred embodiments of the present invention. It should be pointed out that in the detailed description of the embodiments, for simplicity and conciseness, it is impossible for the Description to describe all the features of the practical embodiments in details. It should be understood that in the process of a practical implementation of any embodiment, just as in the process of an engineering project or a designing project, in order to achieve a specific goal of the developer and in order to satisfy some system-related or business-related constraints, a variety of decisions will usually be made, which will also be varied from one embodiment to another. In addition, it can also be understood that although the effort made in such developing process may be complex and time-consuming, some variations such as design, manufacture and production on the basis of the technical contents disclosed in the disclosure are just customary technical means in the art for those of ordinary skilled in the art relating to the contents disclosed in the present invention, which should not be regarded as insufficient disclosure of the present invention.

Unless defined otherwise, all the technical or scientific terms used in the Claims and the Description should have the same meanings as commonly understood by one of ordinary skilled in the art to which the present invention belongs. The terms "first", "second" and the like in the Description and the Claims of the present application for invention do not mean any sequential order, number or importance, but are only used for distinguishing different components. The terms "a", "an" and the like do not denote a limitation of quantity, but denote the existence of at least one. The terms "comprises", "comprising", "includes", "including" and the like mean that the element or object in front of the "comprises", "comprising", "includes" and "including" encompasses the elements or objects and their equivalents illustrated following the "comprises", "comprising", "includes" and "including", but do not exclude other elements or objects. The term "coupled", "connected" or the like is not limited to being connected physically or mechanically, nor limited to being connected directly or indirectly.

Figure 1:
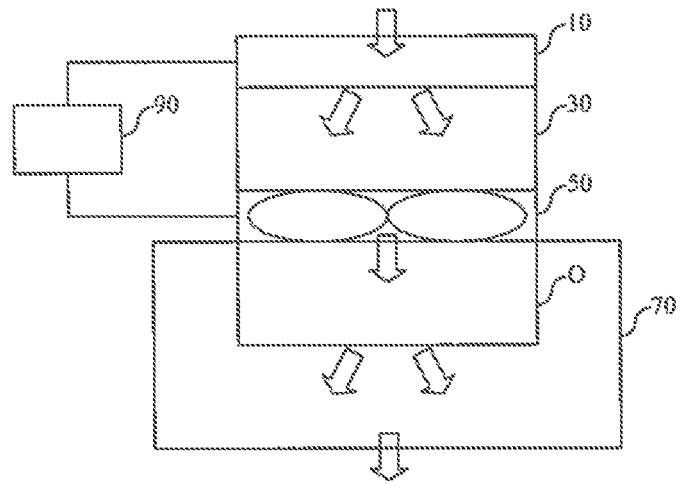
FIG. 1 is a schematic block diagram showing a thermal management system according to an exemplary embodiment.

FIG. 1 is a schematic block diagram of a thermal management system according to an exemplary embodiment. As shown in FIG. 1, the thermal management system may comprise a heater 10, an air mixing portion 30 and a fan 50. The thermal management system may perform a thermal management on a target object O, for example, control a temperature of the target object O.

The heater 10 may be provided at an air inlet of the air mixing portion 30. When exterior air of the thermal management system enters the air mixing portion 30 via the air inlet, the heater 10 may perform heating. The heater 10 herein may be a positive temperature coefficient (PTC) heater that utilizes a PTC element. In one embodiment, the heater 10 may perform heating with a predetermined power, which will be described in details below.

The air mixing portion 30 may provide an air mixing space in which the exterior air that enters into the air mixing portion 30 via the air inlet may be mixed with interior air of the air mixing portion 30. In this way, the exterior air and the interior air may exchange heat sufficiently in the air mixing space. Thus, although the temperature of the exterior air may, for example, abruptly change as the environment temperature changes, since the exterior air is mixed with the interior air and exchanges heat with the interior air in the air mixing portion 30 sufficiently, the change in the temperature of the air supplied to the target object O via an outlet of the air mixing portion 30 may be slow. In other words, the air mixing portion 30 may lengthen a response time of the thermal management system to operate for an external temperature change.

In order to allow the exterior air and the interior air to mix with each other better and to exchange heat with each other better, in one embodiment, the air mixing portion 30 may be configured to have a large enough air mixing space, and/or may include an air guide member. The air guide member may be provided in a path along which the air flows from the air inlet to the air outlet of the air mixing portion, so as to change the direction in which the air flows. In other words, the air guide member may lengthen a time that the air flows from the air inlet to the air outlet. This will be described in more details in the following.

The fan 50 may be provided at the air outlet of the air mixing portion 30. The fan 50 may supply the mixed air in the air mixing portion 30 to the target object O. For instance, in the case that the target object O includes a heat dissipater, the fan 50 may blow the mixed air to the heat dissipater of the target object O. Furthermore, in one exemplary embodiment, the rotation speed of the fan 50 may be controlled according to the temperature of the exterior air, which will be described in more details below.

As mentioned above, the thermal management system in accordance with the exemplary embodiment may supply the air that has been mixed in the air mixing portion to the target object, rather than supply the exterior air after passing the heater to the target object directly. Therefore, a response time of the thermal management system to operate for an external temperature change may be lengthened, thus occurrence of abrupt change in the temperature of the target object as the external temperature changes abruptly may be avoided, improving a reliability of the thermal management system.

According to another exemplary embodiment, the thermal management system may further include a heat maintaining portion 70. As shown in FIG. 1, the heat maintaining portion 70 may be arranged downstream the target object O. In this way, the air supplied to the target object O from the fan 50 may flow into the heat maintaining portion 70 after exchanging heat with the target object O, and eventually be discharged to the outside. The arrows in FIG. 1 illustrate the path in which the air flows in the present exemplary embodiment. The temperature of the heat maintaining portion 70 containing the air flowing from the target object O may be similar to the temperature of the target object O. For example, when the target object O and the thermal management system mounted thereon are in movement (for instance, in rotation), an air flow may be formed in the surrounding air, and such air flow is likely to flow to the target object O. Therefore, the heat maintaining portion 70 may be arranged to be adjacent to the target object O, thereby serving as a buffer element between the target object O and the exterior air that may have a larger temperature difference. Thus, it is possible that the temperature of the target object O is prevented from being affected by the temperature of the exterior air, thereby improving the reliability of the thermal management system. However, the exemplary embodiments are not limited to the above, for example, FIG. 1 schematically shows that the heat maintaining portion 70 may surround the target object O. Under such circumstance, the heat maintaining portion 70 adjacent to the target object O or surrounding the target object O may prevent the target object O from contacting the exterior air directly.

Furthermore, in other exemplary embodiments, the thermal management system may further include a controller 90. The controller 90 may, for example, control the amount of the air supplied to the target object O by controlling the rotation speed of the fan 50. For instance, when the temperature of the exterior air is higher than a desired temperature of the target object O, the controller 90 may control the fan 50 to rotate at a first rotation speed to supply the air to the target object O, and when the temperature of the exterior air is lower than the desired temperature of the target object O, the controller 90 may control the fan 50 to rotate at a second rotation speed higher than the first rotation speed to supply the air to the target object O.

According to the exemplary embodiments, the controller 90 may control the rotation speed of the fan 50 in an asymmetrical manner. Specifically, the controller 90 may control the fan 50 such that an increase amount of the first rotation speed as the temperature of the exterior air rises is larger than a decrease amount of the second rotation speed as the temperature of the exterior air falls.

Figure 2:
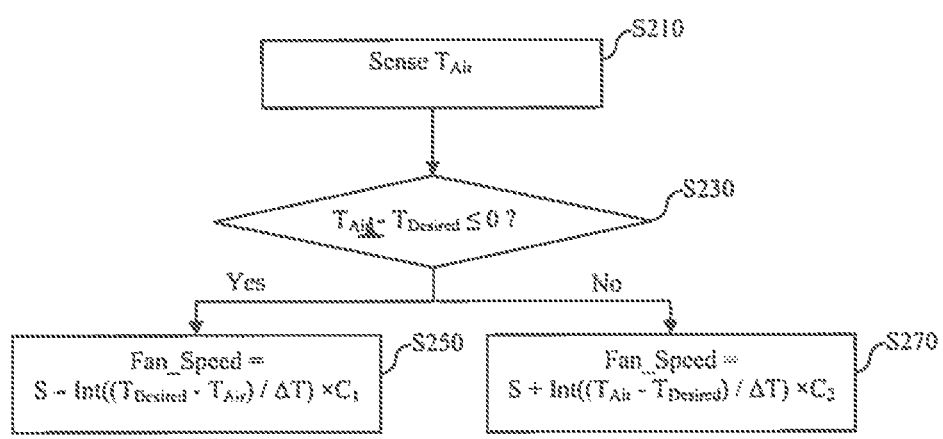
FIG. 2 is a flow chart showing a method for asymmetrically controlling a rotation speed of a fan according to an exemplary embodiment.

FIG. 2 is a flow chart showing a method for asymmetrically controlling a rotation speed of a fan according to an exemplary embodiment. As shown in FIG. 2, first, the temperature of the exterior air $T_{Air}$ may be sensed (S210). To this end, the thermal management system may include a temperature sensor. The temperature sensor may sense the temperature of the exterior air $T_{Air}$, and may send information related to the sensed temperature of the exterior air $T_{Air}$ to the controller 90. Then, it may be determined as to whether the sensed temperature of the exterior air $T_{Air}$ is less than the desired temperature of the target object $T_{Desired}$ (S230). Herein, the desired temperature of the target object $T_{Desired}$ may be set based on the states of the target object. For example, when the target object is an X-ray detector used in a CT apparatus, the desired temperature $T_{Desired}$ may be set to be about 29° C. When the temperature of the exterior air $T_{Air}$ is determined to be less than or equal to the desired temperature of the target object $T_{Desired}$ in the step S230 (i.e., $T_{Air}-T_{Desired} \leq 0$) (S230: Yes), the rotation speed of the fan, Fan_Speed may be controlled in accordance with the following Equation (1) (S250), and when the temperature of the exterior air $T_{Air}$ is determined to be more than the desired temperature of the target object $T_{Desired}$ in the step S230 (S230: No), the rotation speed of the fan, Fan_Speed may be controlled in accordance with the following Equation (2) (S270).

$$\text{Fan\_Speed} = S - \text{Int}((T_{Desired} - T_{Air})/\Delta T) \times C_1 \qquad (1)$$

$$\text{Fan\_Speed} = S + \text{Int}((T_{Air} - T_{Desired})/\Delta T) \times C_2 \qquad (2)$$

Herein, S is the rotation speed of the fan when the temperature of the exterior air $T_{Air}$ is equal to the desired temperature of the target object $T_{Desired}$, $\Delta T$ is a minimum temperature resolution of a monitor for measuring and monitoring the temperature of the target object (or a sensor for sensing the temperature of the target object), $C_1$ and $C_2$ are rotation speed change coefficients, and $C_1 < C_2$ is satisfied. Furthermore, the operator Int( ) means rounding the value within the parentheses.

In one exemplary embodiment, $T_{Desired}$ may be set to be about 29° C., S may be set to be about 1000 RPM, $\Delta T$ may be about 0.125° C., $C_1$ may be set to be 180, $C_2$ may be set to be 1000. According to this embodiment, Equation (1) and Equation (2) may be embodied respectively in:

$$\text{Fan\_Speed} = 1000 - \text{Int}((29 - T_{Air})/0.125) \times 180;$$

$$\text{Fan\_Speed} = 1000 + \text{Int}((T_{Air} - 29)/0.125) \times 1000.$$

Furthermore, the controller 90 may also control a heating power of the heater 10. For example, when the rotation speed of the fan 50 is controlled in the above asymmetrical manner, the controller 90 may control the heater 10 to heat with a desired constant power.

According to the exemplary embodiments, the rotation speed of the fan may be controlled by utilizing an asymmetrical manner, so as to supply to the target object air having amounts corresponding to different temperatures of the exterior air. Thus, a reliability of performing a thermal management on the target object may be improved, reducing temperature fluctuation of the target object. Furthermore, the fan may be controlled to rotate at a slower speed when the temperature of the exterior air is lower than the desired temperature of the target object, thus the noise of the thermal management system may be reduced. Moreover, the heater may be allowed to perform heating with a desired constant power without adding an extra heater or fan, thus the structure of the thermal management system may be simplified, reducing the cost and power consumption of the thermal management system.

Figure 3:
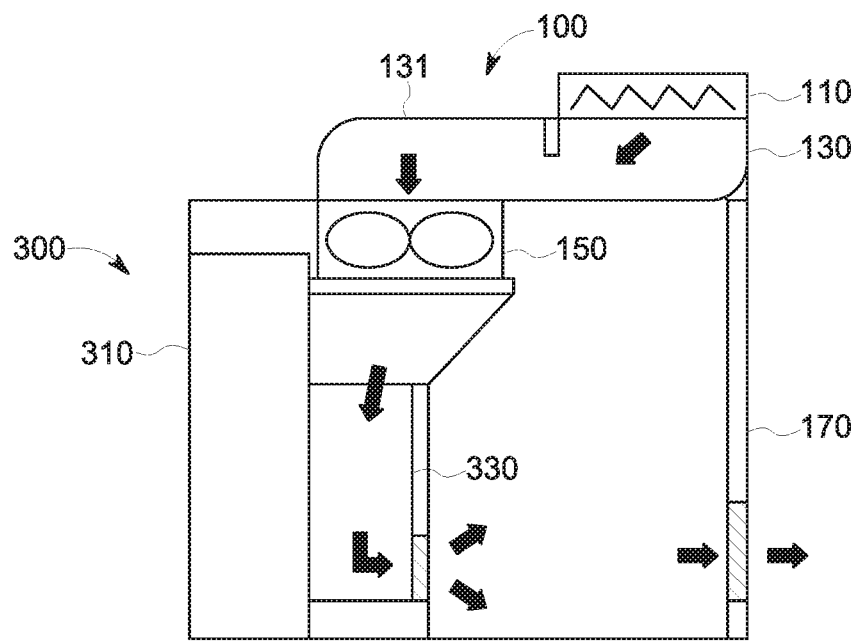
FIG. 3 is a schematic sectional view showing a thermal management system and an X-ray detection device including the thermal management system according to an exemplary embodiment.

FIG. 3 is a schematic sectional view of a thermal management system and an X-ray detection device including the thermal management system according to an exemplary embodiment. As shown in FIG. 3, the X-ray detection device may comprise a thermal management system 100 and an X-ray detector 300.

The thermal management system 100 may comprise a heater 110, an air mixing portion 130 and a fan 150. Furthermore, the thermal management system may further include a heat maintaining portion 170. In other words, the thermal management system 100 may have a construction the same as or similar to that of the thermal management system of the exemplary embodiments as described above, therefore, for sake of conciseness, repeated descriptions for same or similar elements or features will be omitted.

The heater 110 may be provided at an air inlet of the air mixing portion 130, and may heat exterior air of the thermal management system when the exterior air enters the air mixing portion 130 via the air inlet. Herein, the heater 110 may be a PTC heater.

The air mixing portion 130 may provide an air mixing space, as shown in FIG. 3. Thus, although the temperature of the exterior air may, for example, abruptly change as the environment temperature changes, since the exterior air is mixed with the interior air and exchanges heat with the interior air in the air mixing portion 130 sufficiently, the change in the temperature of the air supplied to the X-ray detector 300 as the target object via an outlet of the air mixing portion 130 may be slow. In other words, the air mixing portion 130 may lengthen a response time of the thermal management system 100 to operate for an external temperature change.

The air mixing portion 130 may include an air guide member 131 provided at the air inlet. As shown in FIG. 3, the air guide member 131 may be provided in a path along which the air flows from the air inlet to the air outlet of the air mixing portion. More specifically, the air guide member 131 may be adjacent to the air inlet and positioned downstream the air inlet. Moreover, the air guide member 131 may extend to a predetermined height along a direction substantially perpendicular to a flowing direction in which the air flows from the air inlet to the air outlet, thereby further increasing the time for the flowing air to flow from the air inlet to the air outlet.

The fan 150 may be provided at the air outlet of the air mixing portion 130. The fan 150 may supply the mixed air in the air mixing portion 130 to the X-ray detector 300, e.g., a heat dissipater 330 of the X-ray detector 300. Therefore, the fan 150 may be mounted adjacent to the heat dissipater 330 of the X-ray detector 300.

The heat maintaining portion 170 may be arranged downstream the heat dissipater 330. The air supplied to the heat dissipater 330 from the fan 150 may flow into the heat maintaining portion 170 after exchanging heat with the heat dissipater 330, and eventually be discharged to the outside. The heat maintaining portion 170 is arranged to be adjacent to the heat dissipater 330, e.g., surrounding the heat dissipater 330. Therefore, the heat maintaining portion 170 may serve as a buffer element between the heat dissipater 330 and the exterior air that may have a larger temperature difference. Thus, it is possible that the temperature of the heat dissipater 330 is prevented from being affected by the temperature of the exterior air, thereby improving the reliability of the thermal management system 100.

Although not shown in FIG. 3, the thermal management system 100 according to the exemplary embodiments may include a controller. Herein, the controller may be provided in the thermal management system 100, or may be provided outside the thermal management system 100, and is separated from the other elements of the thermal management system 100. Similar to the controller 90 described in accordance with the above exemplary embodiments, the controller according to the present exemplary embodiment may also control the rotation speed of the fan 150 by utilizing an asymmetrical manner. For example, the controller may perform the method for asymmetrically controlling a rotation speed of a fan as shown in FIG. 2. Moreover, the controller according to the present exemplary embodiment may also control the heater 110 to heat with a desired constant power.

The X-ray detector 300 may comprise an X-ray detection unit 310 and a heat dissipater 330. The X-ray detection unit 310 may convert the incident X-rays to electric signals. The heat dissipater 330 may be provided on the X-ray detection unit 310, e.g., in contact with the X-ray detection unit 310. As mentioned above, the heat dissipater 330 may be positioned downstream the fan 150, so as to exchange heat with the mixed air supplied from the fan 150. In one embodiment, the heat dissipater 330 may include a plurality of heat dissipation fins. Between the plurality of heat dissipation fins, gaps may be formed that allow the air to flow through.

For example, the plurality of heat dissipation fins may be arranged in parallel with the direction in which the air flows.

As mentioned above, the thermal management system and the X-ray detection device including the thermal management system in accordance with the exemplary embodiments may supply the air that has been mixed in the air mixing portion to the X-ray detector, rather than supply the exterior air after passing the heater to the target object directly. Therefore, a response time of the thermal management system to operate for an external temperature change may be lengthened, thus occurrence of abrupt change in the temperature of the X-ray detector as the external temperature changes abruptly may be avoided, improving a reliability of the thermal management system and the X-ray detection device including the thermal management system. Moreover, the rotation speed of the fan may be controlled by utilizing an asymmetrical manner, so as to supply to the target object air having amounts corresponding to different temperatures of the exterior air. Thus, a reliability of performing a thermal management on the X-ray detector may be improved, reducing temperature fluctuation of the target object. Furthermore, the fan may be controlled to rotate at a slower speed when the temperature of the exterior air is lower than the desired temperature of the X-ray detector, thereby the noise of the thermal management system and the X-ray detection device including the thermal management system may be reduced. Moreover, the heater may be allowed to perform heating with a desired constant power without adding an extra heater or fan, thus the structure of the thermal management system and the X-ray detection device including the thermal management system may be simplified, reducing the cost and power consumption of the thermal management system and the X-ray detection device including the thermal management system.

Figure 4:
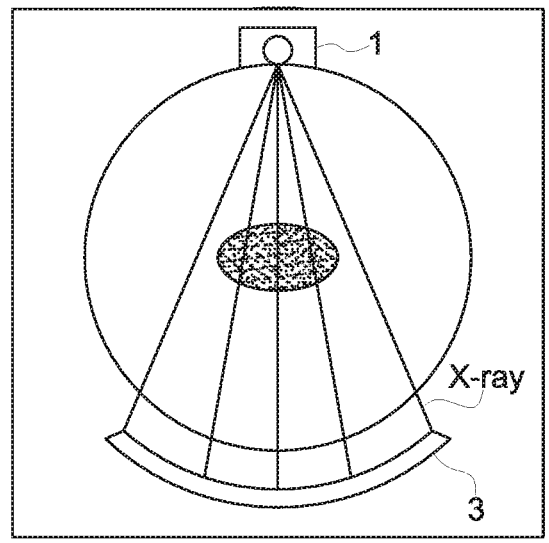
FIG. 4 is a schematic diagram showing a CT apparatus according to an exemplary embodiment.

FIG. 4 is a schematic diagram showing a CT apparatus according to an exemplary embodiment. As shown in FIG. 4, the CT apparatus may comprise an X-ray generation device 1 and an X-ray detection device 3. The X-ray generation device 1 may generate X-rays, and may emit the generated X-rays to an object to be scanned, e.g., a user to be diagnosed. The X-ray detection device 3 may receive the X-rays penetrating the object to be scanned, and may convert the received X-rays to electric signals. Herein, the construction of the X-ray detection device 3 may be the same as that of the X-ray detection device as described above with reference to FIG. 3, for example, the X-ray detection device 3 may comprise a thermal management system and an X-ray detection device. Therefore, for sake of conciseness, repeated descriptions for the same elements or features will be omitted.

Furthermore, although not shown in the figures, the CT apparatus according to the exemplary embodiments may also comprise an image processor for receiving the electric signals converted by the X-ray detection device 3 and processing the received electric signals to obtain an image of the object to be scanned, and a display for displaying the image obtained by the image processor.

As mentioned above, the CT apparatus in accordance with the exemplary embodiments may supply the air that has been mixed in the air mixing portion to the X-ray detector, rather than supply the exterior air after passing the heater to the target object directly. Therefore, a response time of the thermal management system to operate for an external temperature change may be lengthened, thus occurrence of abrupt change in the temperature of the X-ray detector as the external temperature changes abruptly may be avoided, improving a reliability of the CT apparatus. Moreover, the rotation speed of the fan may be controlled by utilizing an asymmetrical manner, so as to supply to the target object air having amounts corresponding to different temperatures of the exterior air. Thus, a reliability of performing a thermal management on the X-ray detector may be improved, reducing temperature fluctuation of the target object. Furthermore, the fan may be controlled to rotate at a slower speed when the temperature of the exterior air is lower than the desired temperature of the X-ray detector, thus the noise of the CT apparatus may be reduced. Moreover, the heater may be allowed to perform heating with a desired constant power without adding an extra heater or fan, thus the structure of the CT apparatus may be simplified, reducing the cost and power consumption of the CT apparatus.

Some exemplary embodiments have been described in the above. However, it should be understood that various modifications may be made thereto. For example, if the described techniques are carried out in different orders, and/or if the components in the described system, architecture, device or circuit are combined in different ways and/or replaced or supplemented by additional components or equivalents thereof, proper results can still be achieved. Accordingly, other embodiments are also falling within the protection scope of the claims.

What is claimed is:

1. A thermal management system, comprising:
a heater;
an air mixing portion; and
a fan, wherein
the heater is provided at an air inlet of the air mixing portion, and is configured to heat air when exterior air enters the air mixing portion via the air inlet,
the air mixing portion is configured to provide an air mixing space for mixing the exterior air that enters the air mixing portion with interior air of the air mixing portion, and
the fan is provided at an air outlet of the air mixing portion, and is configured to supply the mixed air in the air mixing portion to a target object to be thermally managed;
wherein the air mixing portion comprises an air guide member provided in the air mixing space to increase a time for flowing air to flow from the air inlet to the air outlet, the air guide member is positioned downstream of the air inlet and extends from adjacent the air inlet to adjacent the air outlet to define a flow path, and the air guide member is configured to extend along a direction substantially perpendicular to a flowing direction in which the air flows out of the air outlet.

2. The thermal management system according to claim 1, wherein the heater comprises a PTC heater.

3. The thermal management system according to claim 1, wherein the fan is configured to supply the mixed air to a heat dissipater of the target object.

4. The thermal management system according to claim 1, further comprising further comprising a heat maintaining portion, wherein the heat maintaining portion is arranged downstream the target object and adjacent to the target object, and is configured to allow the air passing the target object to flow into the heat maintaining portion.

5. The thermal management system according to claim 4, wherein the heat maintaining portion is configured to surround the target object.

6. The thermal management system according to claim 1, wherein the thermal management system further comprises a controller, the controller is configured to control the fan to rotate at a first rotation speed to supply the air to the target object when a temperature of the exterior air is higher than a desired temperature of the target object, and to control the fan to rotate at a second rotation speed to supply the air to the target object when the temperature of the exterior air is lower than the desired temperature of the target object, wherein the first rotation speed is larger than the second rotation speed.

7. The thermal management system according to claim 6, wherein an increase amount of the first rotation speed as the temperature of the exterior air rises is larger than a decrease amount of the second rotation speed as the temperature of the exterior air falls.

8. The thermal management system according to claim 6, wherein the controller is configured to control a rotation speed of the fan, Fan_Speed in accordance with Equation (1) when the temperature of the exterior air is lower than the desired temperature of the target object, and to control the rotation speed of the fan, Fan_Speed in accordance with Equation (2) when the temperature of the exterior air is higher than the desired temperature of the target object, $$\text{Fan\_Speed}=S-\text{Int}((T\text{Desired}-T\text{Air})/\Delta T)\times C1 \quad (1)$$

$$\text{Fan\_Speed}=S+\text{Int}((T\text{Air}-T\text{Desired})/\Delta T)\times C2 \quad (2)$$

wherein TAir is the temperature of the exterior air, TDesired is the desired temperature of the target object, S is the rotation speed of the fan when the temperature of the exterior air TAir is equal to the desired temperature of the target object TDesired, $\Delta T$ is a minimum temperature resolution of a monitor for monitoring the temperature of the target object, C1 and C2 are rotation speed change coefficients, and C1<C2 is satisfied.

9. The thermal management system according to claim 6, wherein the controller is further configured to control the heater to heat with a desired constant power.

10. The thermal management system according to claim 6, wherein the thermal management system further comprises a temperature sensor, which is configured to sense the temperature of the exterior air.

11. The thermal management system according to claim 1, wherein the thermal management system is configured to manage a temperature of an X-ray detector as the target object.

12. An X-ray detection device, comprising:
an X-ray detector configured to receive X-rays and convert the received X-rays to electric signals; and
a thermal management system configured to perform configured to perform thermal management on the X-ray detector as a target object, the thermal management system comprising a heater, an air mixing portion and a fan, wherein
the heater is provided at an air inlet of the air mixing portion, and is configured to heat air when exterior air enters the air mixing portion via the air inlet,
the air mixing portion is configured to provide an air mixing space for mixing the exterior air that enters the air mixing portion with interior air of the air mixing portion, and
and
the fan is provided at an air outlet of the air mixing portion, and is configured to supply the mixed air in the air mixing portion to the X-ray detector;
wherein the air mixing portion comprises an air guide member provided in the air mixing space to increase a time for flowing air to flow from the air inlet to the air outlet, the air guide member is positioned downstream of the air inlet and extends from adjacent the air inlet to adjacent the air outlet to define a flow path, and the air guide member is configured to extend along a direction substantially perpendicular to a flowing direction in which the air flows out of the air outlet.

13. The X-ray detection device according to claim 12, wherein the X-ray detector comprises a heat dissipater, which is arranged downstream of the fan and which includes a plurality of heat dissipation fins, so as to exchange heat with the mixed air supplied from the fan.

14. A CT apparatus, comprising:
an X-ray generation device configured to generate X-rays and emit the generated X-rays to an object to be scanned; and
an X-ray detection device configured to receive the X-rays penetrating the object to be scanned and convert the received X-rays to electric signals, the X-ray detection device comprising
a thermal management system configured to perform thermal management on the X-ray detection device as a target object, the thermal management system comprising a heater, an air mixing portion, and a fan, wherein
the heater is provided at an air inlet of the air mixing portion, and is configured to heat air when exterior air enters the air mixing portion via the air inlet,
the air mixing portion is configured to provide an air mixing space for mixing the exterior air that enters the air mixing portion with interior air of the air mixing portion, and
the fan is provided at an air outlet of the air mixing portion, and is configured to supply the mixed air in the air mixing portion to the X-ray detection device;
wherein the air mixing portion comprises an air guide member provided in the air mixing space to increase a time for flowing air to flow from the air inlet to the air outlet, the air guide member is positioned downstream of the air inlet and extends from adjacent the air inlet to adjacent the air outlet to define a flow path, and the air guide member is configured to extend along a direction substantially perpendicular to a flowing direction in which the air flows out of the air outlet.

* * * * *